United States Patent
Freeman

(10) Patent No.: US 11,672,730 B2
(45) Date of Patent: *Jun. 13, 2023

(54) CHEST COMPLIANCE DIRECTED CHEST COMPRESSIONS

(71) Applicant: ZOLL Medical Corporation, Chelmsford, MA (US)

(72) Inventor: Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 56 days.

This patent is subject to a terminal disclaimer.

(21) Appl. No.: 17/342,876

(22) Filed: Jun. 9, 2021

(65) Prior Publication Data

US 2021/0369560 A1 Dec. 2, 2021

Related U.S. Application Data

(63) Continuation of application No. 15/267,255, filed on Sep. 16, 2016, now Pat. No. 11,058,602.
(Continued)

(51) Int. Cl.
*A61H 31/00* (2006.01)
*G16H 20/30* (2018.01)
*G16H 20/40* (2018.01)

(52) U.S. Cl.
CPC ......... *A61H 31/007* (2013.01); *A61H 31/005* (2013.01); *G16H 20/30* (2018.01);
(Continued)

(58) Field of Classification Search
CPC .... A61H 31/00; A61H 31/004; A61H 31/005; A61H 31/006; A61H 31/007;
(Continued)

(56) References Cited

U.S. PATENT DOCUMENTS

| 4,797,104 A | 1/1989 | Laerdal |
| 6,463,327 B1 | 10/2002 | Lurie |

(Continued)

FOREIGN PATENT DOCUMENTS

| CN | 101303812 A | 11/2008 |
| CN | 101534783 A | 9/2009 |

(Continued)

OTHER PUBLICATIONS

Basseville et al. (1993) "Detection of Abrupt Changes—Theory and Application", Prentice Hall, 469 pages.
(Continued)

*Primary Examiner* — Timothy A Stanis
*Assistant Examiner* — Matthew R Moon
(74) *Attorney, Agent, or Firm* — Mintz Levin Cohn Ferris Glovsky and Popeo, P.C.

(57) ABSTRACT

Among other things, in one aspect, we describe a system for assisting with cardiopulmonary resuscitation (CPR). The system includes at least one sensor; and one or more processors configured for calculating a chest compliance relationship based on data received from the at least one sensor, and determining a neutral position of chest compression based at least in part on a feature of the chest compliance relationship. The system can take the form of an active compression-decompression device.

75 Claims, 12 Drawing Sheets

Related U.S. Application Data

(60) Provisional application No. 62/221,167, filed on Sep. 21, 2015.

(52) U.S. Cl.
CPC ....... *G16H 20/40* (2018.01); *A61H 2031/001* (2013.01); *A61H 2201/0184* (2013.01); *A61H 2201/123* (2013.01); *A61H 2201/1253* (2013.01); *A61H 2201/1619* (2013.01); *A61H 2201/1635* (2013.01); *A61H 2201/5007* (2013.01); *A61H 2201/5043* (2013.01); *A61H 2201/5048* (2013.01); *A61H 2201/5061* (2013.01); *A61H 2201/5064* (2013.01); *A61H 2201/5071* (2013.01); *A61H 2201/5084* (2013.01); *A61H 2201/5097* (2013.01); *A61H 2230/04* (2013.01)

(58) Field of Classification Search
CPC ............ A61H 31/008; A61H 2031/001; A61H 2201/1207; A61H 2201/50; A61H 2201/5058; A61H 2201/5061
See application file for complete search history.

(56) References Cited

U.S. PATENT DOCUMENTS

| | | | |
|---|---|---|---|
| 8,652,007 B2 | 2/2014 | Centon | |
| 8,920,348 B2 | 12/2014 | Freeman | |
| 9,358,178 B1 | 6/2016 | Morgan | |
| 9,713,568 B2 | 7/2017 | Nilsson | |
| 11,052,019 B2* | 7/2021 | Freeman | A61H 31/005 |
| 11,058,602 B2* | 7/2021 | Freeman | G16H 20/40 |
| 2002/0188332 A1 | 12/2002 | Lurie et al. | |
| 2002/0193711 A1 | 12/2002 | Halperin et al. | |
| 2004/0249297 A1 | 12/2004 | Pfeiffer et al. | |
| 2004/0267325 A1 | 12/2004 | Geheb et al. | |
| 2007/0050910 A1 | 3/2007 | Blanchard et al. | |
| 2008/0300517 A1 | 12/2008 | Nysaether | |
| 2008/0300518 A1 | 12/2008 | Bowes | |
| 2012/0052470 A1 | 3/2012 | Woerlee et al. | |
| 2012/0136286 A1 | 5/2012 | Nova | |
| 2012/0330200 A1* | 12/2012 | Voss | A61H 31/004 601/41 |
| 2013/0218056 A1 | 8/2013 | Aelen | |
| 2013/0282068 A1 | 10/2013 | Sagiroglu et al. | |
| 2013/0324894 A1 | 12/2013 | Herken | |
| 2013/0330200 A1 | 12/2013 | Merz | |
| 2014/0046228 A1 | 2/2014 | Walker | |
| 2014/0100496 A1 | 4/2014 | Johnson et al. | |
| 2014/0121574 A1 | 5/2014 | Chladek | |
| 2014/0257054 A1 | 9/2014 | Packer et al. | |
| 2014/0323928 A1 | 10/2014 | Johnson | |
| 2015/0257971 A1 | 9/2015 | Chapman | |
| 2016/0136042 A1* | 5/2016 | Nilsson | A61H 31/006 601/41 |
| 2017/0105895 A1 | 4/2017 | Taylor | |
| 2018/0092803 A1 | 4/2018 | Freeman et al. | |
| 2018/0092804 A1 | 4/2018 | Hunt et al. | |

FOREIGN PATENT DOCUMENTS

| | | |
|---|---|---|
| CN | 102368991 A | 3/2012 |
| CN | 102920588 A | 2/2013 |
| CN | 103200920 A | 7/2013 |
| CN | 104271103 A | 1/2015 |
| JP | 2005046606 A | 2/2005 |
| JP | 2005046609 A | 2/2005 |
| WO | 9925306 A1 | 5/1999 |

OTHER PUBLICATIONS

Lobdell et al. (1973) "Impact Response of the Human Thorax", Human Impact Response, 45 pages.

Jalali et al., "Modeling Mechanical Properties of the Chest During the Cardiopulmonary Resuscitation Procedure", Computing in Cardiology, vol. 41:13-17 (2014).

PCT Notification of Transmittal of the International Search Report and the Written Opinion of the International Searching Authority, or the Declaration for International Application No. PCT/US16/52053, dated Dec. 7, 2016, 10 pages.

* cited by examiner

CHEST COMPLIANCE DIRECTED CHEST COMPRESSIONS

CLAIM OF PRIORITY

This application is a continuation of U.S. application Ser. No. 15/267,255, filed on Sep. 16, 2016, which claims benefit of priority under 35 USC § 119(e) to U.S. Provisional Application Ser. No. 62/221,167, filed on Sep. 21, 2015, the entire contents of which are hereby incorporated by reference.

TECHNICAL FIELD

This invention relates to the field of cardiac resuscitation, and in particular to devices for assisting rescuers in performing active compression and decompression of the chest during cardio-pulmonary resuscitation (CPR).

BACKGROUND

Worldwide, sudden cardiac arrest is a major cause of death and is the result of a variety of circumstances, including heart disease and significant trauma. In the event of a cardiac arrest, several measures have been deemed to be essential in order to improve a patient's chance of survival. These measures, termed Cardiopulmonary Resuscitation (CPR) must be taken as soon as possible to at least partially restore the patient's respiration and blood circulation. CPR is a collection of therapeutic interventions designed to both provide blood flow via external manipulation of the external surface of the patient (e.g. thorax, abdomen, legs) as well as oxygenate the patient's blood, typically via delivery of external oxygen and other gases to the patient's lungs. One common technique, developed approximately 30 years ago, is chest compression.

Chest compression during CPR is used to mechanically support circulation in subjects with cardiac arrest, by maintaining blood circulation and oxygen delivery until the heart is restarted. The victim's chest is compressed by the rescuer, ideally at a rate and depth of compression in accordance with medical guidelines, e.g., the American Heart Association (AHA) guidelines. Other key chest compression parameters are velocity of decompression or release velocity, and the duty cycle of compression and decompression phases.

Traditional chest compressions are performed by the rescuer by laying the patient on their back, placing the rescuer's two hands on the patient's sternum and then compressing the sternal area downward towards the patient's spine in an anterio-posterior direction with an applied downward force. The rescuer then raises their hands upwards and releases them from the patient's sternal area, and the chest is allowed to expand by its natural elasticity that causes expansion of the patient's chest wall. The rescuer then repeats this down-and-up motion in a cyclical, repetitive fashion at a rate sufficient to generate adequate blood flow. The downward phase of the compression is typically referred to as the compression phase. The upward-going portion of the compression cycle is typically referred to as the release or decompression phase.

One key step for creating blood flow through the heart is to release the chest adequately after each chest compression. The chest should be released sufficiently to enhance negative pressure in the thoracic cavity, to facilitate venous filling of the ventricles of the heart and increase blood volume available to be distributed during the next chest compression. If the chest is not released adequately, venous return and right atrial filling will be hindered.

In order for the rescuer to properly deliver chest compressions, it is beneficial to be able to provide real-time feedback to rescuer's that allow them to adjust the various aspects of their compressions to deliver optimal care to the patient. Systems such as the ZOLL Medical RealCPRHelp (Chelmsford Mass.) use accelerometers or other motion sensors to measure the motion of the patient's sternum and provide real-time feedback on chest compression parameters such as those mentioned above. The sternal motion is also stored in the monitoring device—a defibrillator or even a smartphone, smartwatch, etc.—for review by the rescuer or other medical personnel. Some systems use just force sensors to estimate the chest compression motion parameters by assuming some nominal value for the patient's chest compliance and calculating an estimated displacement from the measured force.

In order to increase cardiopulmonary circulation induced by chest compression, a technique referred to as active compression-decompression (ACD) has been developed. According to ACD techniques, an applicator body is interposed between the rescuer's hands and the patient's sternum, the applicator body further being affixed via a suction cup or cups or self-adhesive pad. During the compression phase, the rescuer presses against the applicator pad to compress the patient's sternum, as with standard chest compressions. Unlike standard chest compressions where the chest passively returns to its neutral position during the release phase, with ACD, the rescuer actively pulls upward during release or decompression phase. This active pulling upward, or active decompression, increases the release velocity and results in increased negative intrathoracic pressure, as compared to standard chest compressions, and induces enhanced venous blood to flow into the heart and lungs from the peripheral venous vasculature of the patient. Devices and methods for performing ACD to the patient are described in U.S. Pat. Nos. 5,454,779 and 5,645,552.

During ACD chest compression, the patient's sternum is typically pulled upward beyond the neutral position of the sternum during the decompression phase, where "neutral" is defined as the steady-state position of the sternum when no force—either upward or downward—is applied by the rescuer. As will be described below with respect to FIG. 3, both the compression phase and decompression phase will both have a portion of their motion during which the sternum is pulled upward beyond the neutral position—what we term the "Elevated" phase. There are thus 4 phases: Compression: Elevated (CE); Compression: Non-elevated (CN); Decompression: Elevated (DE); Decompression: Non-elevated (DN). It is beneficial to be able to provide real-time feedback to the rescuer on these different phases of the Active Compression Decompression cycle.

During the time-course of a resuscitation, the patient's chest wall will "remodel" as a result of the repetitive forces applied to the chest wall—sometimes exceeding 100 lbs of force needed to sufficiently displace the sternum for adequate blood flow—and the resultant repetitive motion. Chest compliance will typically increase significantly as the sternum/cartilage/rib biomechanical system is substantially flexed and stressed. Thus the amount of force needed to displace the sternum to the proper compression and decompression depths will also change significantly. During the course of chest wall remodeling, the anterior-posterior diameter—the distance between the sternum and the spine—will also very frequently alter substantially, meaning the neutral position will change over the course of the resuscitation. An accurate measure of the neutral position is needed at all times during the course of the resuscitation; thus, taking an initial position measurement at the beginning of the resuscitation and assuming a constant neutral position over the course of the resuscitation will not be sufficient to generate accurate estimations of the motion parameters of the CE, CN, DE and DN phases of the compression cycle. For instance, it is of particular value to be able to measure the motion parameters and forces delivered during the DE phase and CN phases independently from each other and to the exclusion of the CE and DN phases.

Some ACD systems use a force sensor interposed between the rescuer's hands and the patient's sternum, where compressions are being delivered, to monitor the relaxation phase of the chest compression. However, the sternal force for a chest compression does not correlate to blood flow, nor does it correlate with sternal motion or chest wall dynamics. Each patient requires a unique amount of force to achieve the same compression of the sternum and the cardiopulmonary system due to the widely varying compliances of individual patients' chests. Further, a force sensor is generally not able to measure motion of the sternum—a key parameter for understanding the quality of the chest compression delivered and the amount of venous return.

Other chest compression monitoring systems that utilize motion-sensing systems such as accelerometers; for instance, the ZOLL Medical RealCPRHelp (Chelmsford Mass.), are able to measure motion parameters such as velocity and displacement. However, because of the way that ACD compressions are delivered, existing systems are limited in their ability to distinguish between the motions of the Elevated and Non-elevated phases.

SUMMARY

Among other things, in one aspect, we describe a system for assisting with cardiopulmonary resuscitation (CPR). The system includes at least one sensor; and one or more processors configured for calculating a chest compliance relationship based on data received from the at least one sensor, and determining a neutral position of chest compression based at least in part on a feature of the chest compliance relationship. The system can take the form of an active compression-decompression device.

The system has a number of advantages. For example, the system can provide feedback (e.g., on a user interface) that allows a rescuer to understand the effectiveness of the CPR treatment he or she is administering. The rescuer can then adjust the forces that he or she is applying during the CPR treatment and receive feedback confirming whether the adjustment is improving the effectiveness of the treatment. Depending on the implementation, the feedback can be provided by a CPR device, or transmitted to a second device external to the CPR device. In this way, it is more likely the CPR treatment will be effective at resuscitating the victim, and less likely that the CPR treatment will cause injury to the victim.

The details of one or more implementations are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
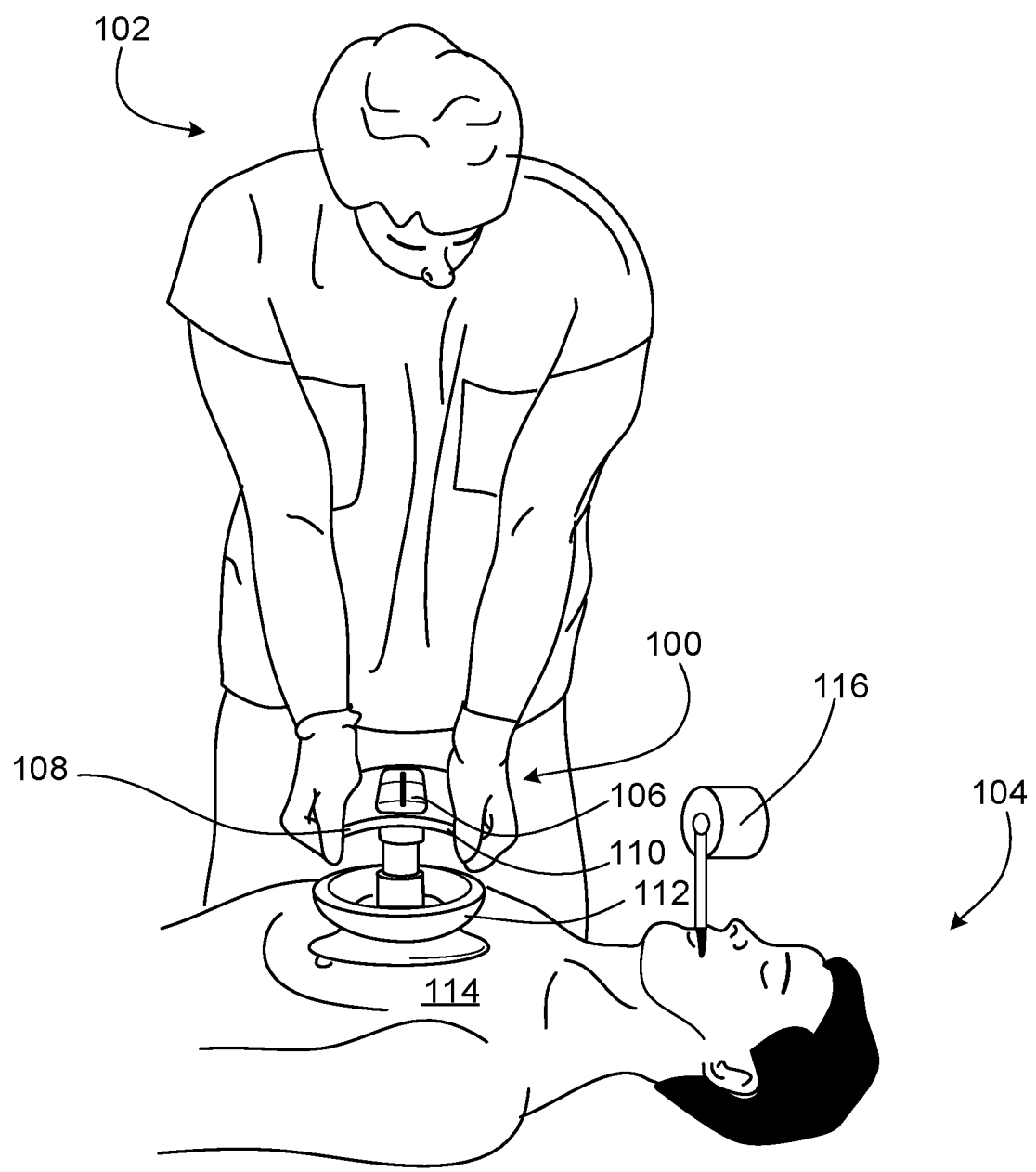
FIG. 1 is shows a device that assists a user with performing active compression-decompression (ACD) CPR on a patient.

FIG. 1 shows a device 100 that assists a user 102 with performing active compression-decompression (ACD) CPR on a patient 104 who is being rescued from a cardiac event. The device 100 includes a user interface 106 that provides feedback to the user 102 (sometimes referred to as a rescuer) about the effectiveness of the CPR that the user 102 is administering. The feedback is determined based on part on information about chest compliance of the patient 104 (sometimes referred to as a victim) as measured by the device 100 (sometimes referred to as an ACD device).

Chest compliance is a measure of the ability of the chest to absorb an applied force and change shape in response to the force. In the context of CPR, information about chest compliance can be used to determine how force can be applied to the chest of a patient in a way that will be effective at resuscitating the patient. Ideally, the force applied to the patient will be sufficient to create a vacuum within the heart that causes blood to flow. However, if the force is not sufficient to create this vacuum, CPR will not be effective and the patient will die or otherwise deteriorate. Further, if the force is not applied correctly or is too great, then the patient may be injured. Feedback provided to the user 102 can be enhanced by determining a neutral position of chest compression and using information about the administration of the CPR treatment to give the user 102 guidance that will improve the chances of success of the CPR treatment.

The neutral position location or other phase transition points may be determined by methods described herein. The neutral position may also be considered the position at which zero force or pressure is exerted by the rescuer during ACD compressions. Because of so-called chest remodeling that occurs during chest compressions, this zero-force neutral position may change over the course of resuscitation efforts, as the anterior/posterior diameter of the patient will decrease after multiple compression cycles. Alternatively, the neutral position location may be simply the initial position of the sternum prior to initiation of chest compressions.

In some implementations, the device 100 determines (e.g., calculates) a chest compliance relationship that is then used to determine what feedback to provide the user. For example, the device 100 may calculate a mathematical relationship between two variables, such as displacement and force, related to chest compliance. The device 100 can then identify one or more features of this relationship that can be used to determine information about the CPR treatment. Once the information about the CPR treatment is determined, the device 100 can determine what feedback to provide to the user, e.g., feedback about the progress of the CPR treatment, feedback related to chest compression depth when in the non-elevated portion of the chest compression cycle or feedback related to the force when in the elevated portion of the chest compression cycle.

In some examples, the information about the CPR treatment can include information about the patient such as a neutral position of chest compression. In some implementations, the chest compliance relationship can be thought of or represented as a curve, e.g., a curve of a graph representing the relationship. In some implementations, the chest compliance relationship can be stored as data such as a table of measured values (e.g., values for displacement and force at multiple time indices).

As shown in FIG. 1, the device 100 has handles 108, 110 that the user 102 grips to apply force. The device 100 also has a suction cup 112 that tends to keep the device 100 in contact with the chest 114 of the patient 104. When the user applies upward force using the device 100, the chest 114 of the patient will be pulled upward in response due to the suction of the suction cup 112. This upward force creates a negative pressure within the thorax of the patient during the release phase of a CPR treatment. A device that creates a negative pressure in this way is sometimes referred to as an impedance threshold device (ITD) 116.

In some examples, the feedback given to the user 102, e.g., on the user interface 106, guides the user in the way that the user 102 is compressing the chest using the device 100. For example, the user interface 106 can include a visual indication of the effectiveness of the upward and downward portions of the compression cycle. Parameters for which feedback can be provided include compression depth and compression release velocity. In this way, the user 102 can adjust the various elements of their compression activity in response to the feedback.

As a real-world example, the user interface 106 may display a graph that shows whether the upward or downward forces are too strong, or not strong enough, and then the user 102 can adjust accordingly. For example, if the device 100 determines that the depth of the compression phase is not sufficient for an effective CPR treatment, the device 100 can display feedback indicating that the depth of the downward motion is not meeting a threshold of effectiveness. In some implementations, the device 100 can determine whether the upward or downward forces are too strong or not strong enough based on an estimate of the neutral position of chest compression of the patient 104. The neutral position of chest compression of the patient 104 serves as an inflection point that can be used to differentiate the movement of the chest on upward strokes from movement of the chest on downward strokes and generate specific measurements for the CE, CN, DN and DE phases of the compression cycle.

Because the user 102 manually delivers a compression, the ACD device 100 shown here is an example of a manual ACD device. Other types of mechanical ACD devices can be used with the techniques described below, e.g., the techniques for determining a neutral position of chest compression. Although the ACD device 100 shown here includes a handle and a suction cup, other types of ACD devices used with the techniques described below need not include these elements. For example, other types of ACD devices may include a first element configured to be affixed to a surface of a patient's body and a second element configured to be coupled to a hand of a rescuer. In these examples, the first element allows for pulling upward on the patient's body surface while maintaining contact with the patient's body surface. Further, in these examples, the second element enables the rescuer to push on the chest and pull up the chest.

A suction cup and handle are examples of the first element and the second element, respectively, but are not the only types of these elements that can be used. For example, the first element could include one or more assemblies of multiple suction cups, or the first element could be a surface partially or fully covered by an adhesive (e.g., adhesive gel) that affixes to a patient's chest, or the first element could be a combination of any of these things. Examples of assemblies of multiple suction cups are described in U.S. Pat. No. 8,920,348, titled "Method and Device for Performing Alternating Chest Compression and Decompression," incorporated by reference in its entirety. The second element could include one or more straps or brackets that hold the rescuer's hand tightly against the ACD device, instead of or in addition to the handle described above.

Figure 2:
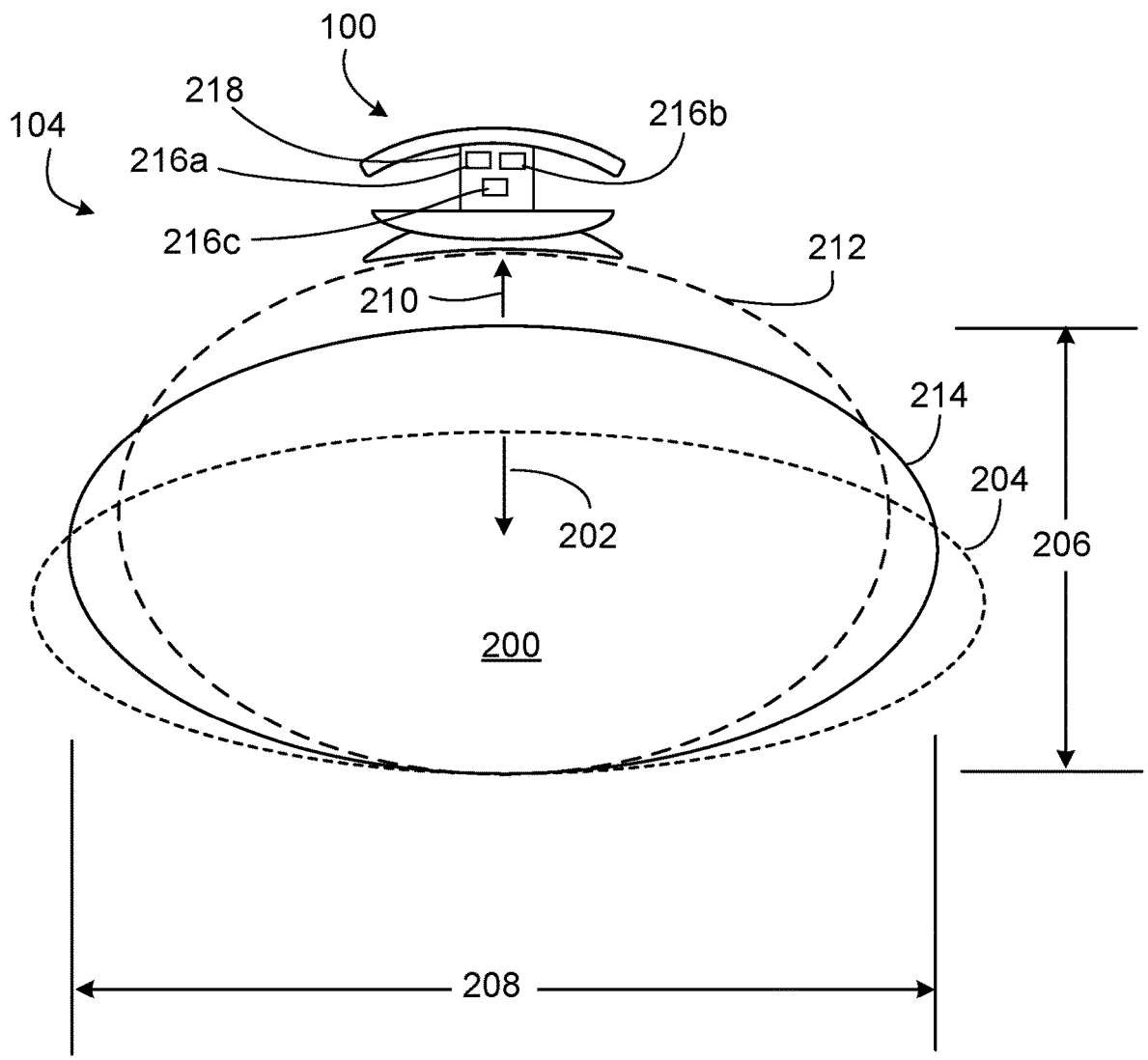
FIG. 2 represents the change in shape of the chest of a patient.

FIG. 2 represents the change in shape of the chest 200 of a patient 104 as the ACD device 100 is used to perform ACD CPR. Because the chest 200 of a human being is not rigid, the chest will change shape in response to forces applied. When the sternum is compressed downward 202 in the CN phase, the chest 200 tends to exhibit a shape 204 that is compressed in the anterior-posterior (AP) dimension 206 and extended in the lateral dimension 208. This shape 204 is sometimes referred to as a compression shape. During the DE phase 210, the chest 200 tends to exhibit a shape 212 that is extended in the AP dimension 206 and narrower in the lateral dimension 208. This shape 212 is sometimes referred to as a decompression shape. The chest 200 exhibits a shape 214 corresponding to a neutral position of chest compression, when no force is applied either upwards or downwards. In other words, the shape 214 corresponds to the natural position of the chest when its shape is not substantially affected by a force applied, e.g., during CPR chest compressions.

Figure 3:
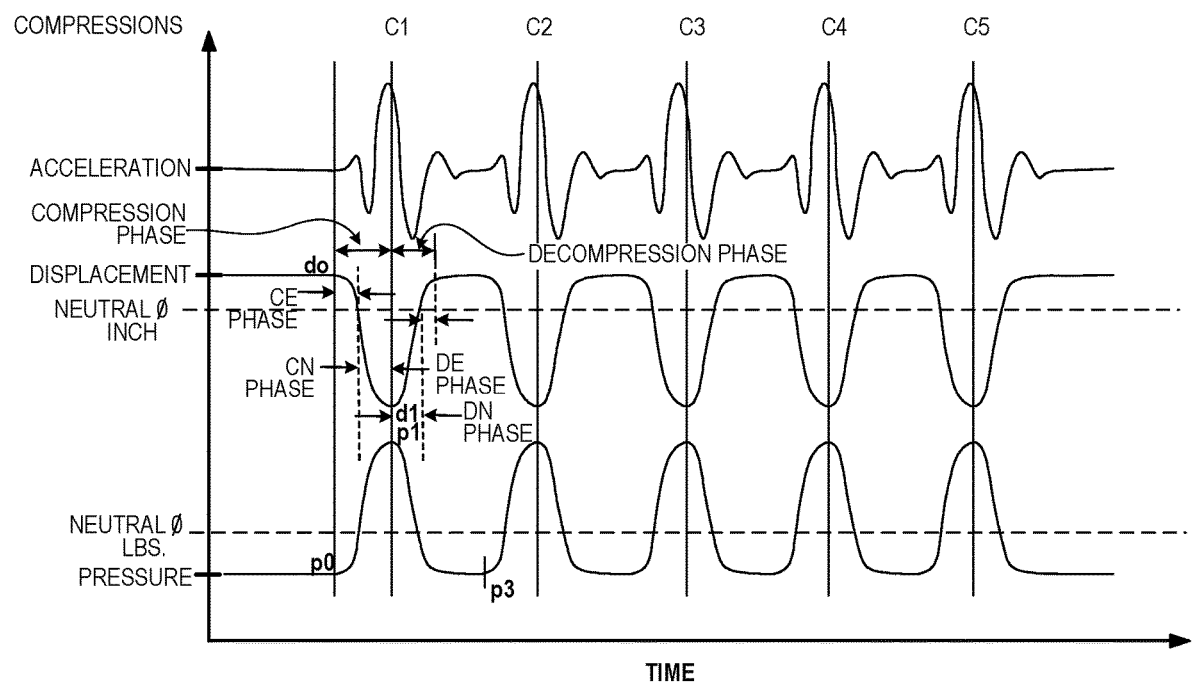
FIG. 3 represents signals recorded during CPR.
Figure 5:
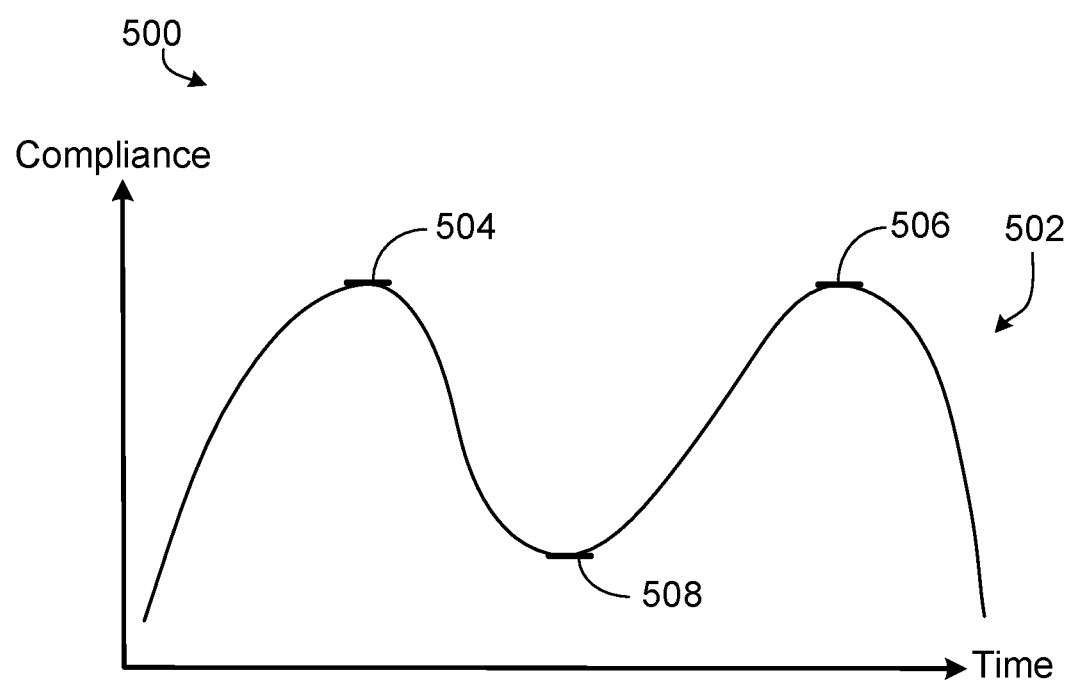
FIG. 5 shows an example graph including a chest compliance curve.

Chest compliance is the mathematical description of this tendency to change shape as a result of an applied force. It is the inverse of stiffness. It is the incremental change in depth divided by the incremental change in force at a particular instant in time. In the case of a chest compression cycle, the compliance may be plotted with time on the abscissa as shown in FIG. 3, or alternatively, the compliance may be plotted as a loop with depth as the independent variable and the time variable implied in the loop trajectory, as shown in FIGS. 5 and 6. If a patient's chest exhibits relatively little change in shape in response to a particular change of force, the patient has relatively low chest compliance. In contrast, if the patient's chest exhibits relatively high change in shape in response to a particular change of force, the patient has relatively high chest compliance. In addition, chest compliance varies as the chest is compressed as a result of the structural changes of the thoracic cavity due to positional/conformational changes as the chest is compressed downwards and pulled upwards. This is described below with respect to FIGS. 5 and 7. For example, as the chest is compressed downward, the compliance of the chest decreases as the chest approaches the limits of its flexibility, e.g. region 508 or the flat region on the right side of the curve of FIG. 7.

For each point in time, n, for which a displacement measurement is taken by the system, a force measurement is also taken, resulting in a displacement/force vector-pair for each sample time n, $[d_n, f_n]$. In general, compliance, c, equals the change in displacement divided by the change in pressure, compared to a reference time point: $c = \Delta d / \Delta p$.

"Instantaneous Compliance" (IC) refers to when the reference time point, $t_0$, is adjacent or nearly adjacent to the time point, $t_0$, and is thus more a measure of the slope of the displacement-force curve, at a particular point in time. For instance, the reference time point, $t_0$, may be the sample time point immediately preceding time, $t_n$. The reference time point may be composed on multiple sample points immediately preceding time, $t_n$, for instance using a moving average, weighted moving average or low pass filter, known to those skilled in the art. There may be a small gap in time between the reference time point and time, $t_n$, for instance 1 second or less. In some versions, the reference time point may be chosen to be the beginning of a segment, for instance the beginning of the compression for Slope 1 (the first segment in the compression, and thus the segment start is also the compression start) in FIG. 6B or the dotted line for reference time $t_0$ for Slope 2 in the same figure.

$$\text{Instantaneous Compliance InC}_n = |(d_n - d_r)/(p_n - p_r)|$$

Where $InC_n$ is the estimate of the slope of the distance/pressure curve at a point in time, $t_n$; $d_n$ is the displacement at time, $t_n$; $p_p$ is the pressure at time $t_n$; and $d_r$ and $p_r$ are the distance and pressure at the reference time, $t_r$, respectively.

"Absolute Compliance" (AC), on the other hand, refers to when the reference point, $t_0$, uses an absolute reference such as the pressure and displacement at the very start of a group of chest compressions. During CPR, there may be what are termed "rounds" of chest compressions which are periods of approximately 1-3 minutes where chest compressions are delivered, and then at the end of the time period, compressions are halted and various other therapeutic actions may be performed, such as analyzing the patients ECG, delivering a defibrillation shock or delivering a drug such as epinephrine or amiodarone. Thus for determination of AC, reference point, $t_0$, prior to the beginning of any of the rounds of chest compressions, including prior to the first round of compression, i.e. at the beginning of CPR. In most instances, the pressure will be zero at this point in time, and the displacement will be effectively calibrated to zero by the displacement estimation software. The Absolute Compliance of the chest can be estimated from the compression displacement and the related compression pressure. The reference pressure "$p_0$" is the pressure at time, $t_0$, and chest displacement "$d_0$" is the displacement at time, $t_0$. The pressure "$p_n$" is the pressure required to achieve the displacement "$d_n$". The chest compliance is estimated from the following equation:

$$\text{Absolute Compliance} = |(d_p - d_0)/(p_p - p_0)|$$

Where $d_p$ is the displacement at the peak of the compression and $p_p$ is the pressure at the peak of the compression.

The compliance and compression depth of the chest 200 can be measured by sensors 216*a-c* in the device 100. For example, a force sensor 216*a* and a motion sensor such as an accelerometer 216*b* can be used. In some implementations, the force sensor 216*a* and the accelerometer 216*b* are placed in a housing 218 of the device 100. The accelerometer senses the motion of the chest during CPR and the force sensor measures the force or pressure applied. The accelerometer signal is integrated to determine the displacement of the housing 218, and the output of the force sensor is converted to standard pressure or force units.

In some implementations the accelerometer is in a separate housing, for example a housing placed on the sternum of the patient, and the force sensor is in a housing, e.g. housing 218 of the device 100. In such an implementation the housing containing the accelerometer and the device with the force sensor may be configured to be attached or connected during CPR.

In some implementations, multiple accelerometers 216*b*, 216*c* can be used. For example, the second accelerometer 216*c* can be placed on the patient's sternum in the inner perimeter or near the suction cup 112. The second accelerometer may be contained in a separate assembly of self-adhesive foam such as the ZOLL CPR Stat-Padz (Chelmsford, Mass.). In this way, the first accelerometer 216*b* tends to measure acceleration experienced by the rescuer's hands 102 (FIG. 1), and the second accelerometer 216*c* tends to measure acceleration of the patient's sternum 104. Put another way, the first accelerometer 216*a* may be configured to measure movement arising from an applied upward force, e.g., because the first accelerometer 216*a* is proximate or otherwise mechanically coupled to the suction cup 112, it provides a suitable indication of force applied as the suction cup 112 pulls up on the patient's sternum. Further, the second accelerometer 216*b* may measure movement arising from an applied downward force, e.g., because the second accelerometer 216*b* is proximate or otherwise mechanically coupled to the handle of the device 100, the second accelerometer 216*b* provides a suitable indication of downward force applied by the rescuer's hand. In this fashion, the system can detect if the is insufficient adherence between the ACD device and the patient's sternum and alert the rescuer to re-apply the ACD device to the patient's chest.

FIG. 3 represents signals recorded during CPR, e.g., using the sensors 214*a-c* shown in FIG. 2. Though Absolute Compliance may be used to determine the neutral position, InC will provide a more accurate measure of the neutral position.

Compressions (C1-C5) can be detected from the displacement signal. The compression rate is calculated from the interval between compressions (e.g. (time of C2–time of C1)), and compression depth is measured from the compression onset to peak displacement (e.g. (d1–d0)). The onset and peak compression values are saved for each compression. The pressures at the compression onset and offset are used to determine the force used to achieve a given compression depth. Chest compliance is further described in U.S. Pat. No. 7,220,235, titled "Method and Apparatus for Enhancement of Chest Compressions During CPR," issued May 22, 2007, and is hereby incorporated by reference in its entirety. Compression velocity and displacement can be estimated via such methods as described in U.S. Pat. Nos. 8,862,228, 6,827,695, and 6,390,996, each hereby incorporated by reference in its entirety.

Figure 4:
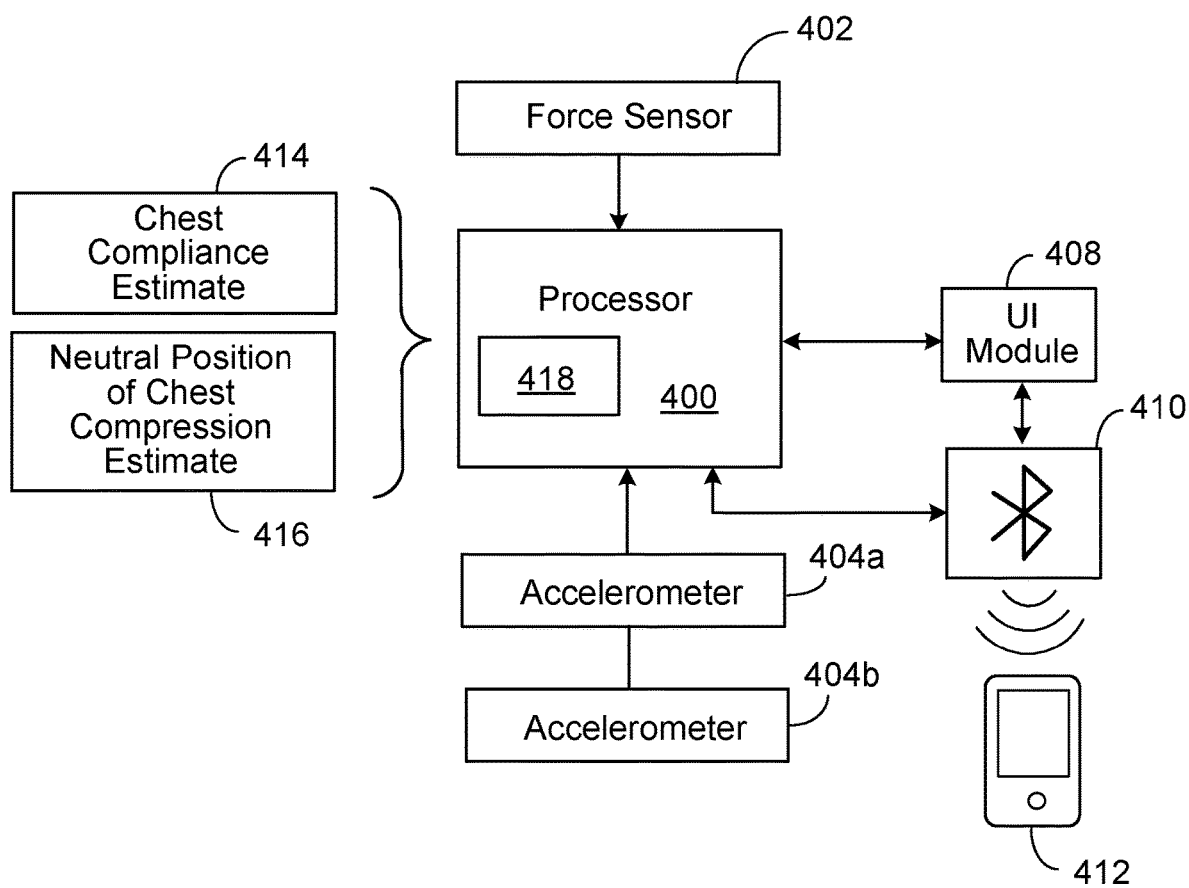
FIG. 4 is a block diagram of components of the ACD device shown in FIG. 1.

FIG. 4 is a block diagram of components of the ACD device 100 shown in FIG. 1. The device includes a processor 400, e.g., an electronic component such as a microprocessor that carries out instructions, e.g., processes input data to generate output data, and communicates data to and from other components of the device 100. For example, the processor 400 receives signals from sensors such as the force sensor 402 and motion sensors such as accelerometers 404*a*, 404*b* (or, in some implementations, a single accelerometer). Other types of motion sensors may include magnetic induction based systems such as described in U.S. Pat. No. 7,220,235, mentioned above.

The processor 400 also communicates output information 406 to a user interface module 408. The output information 406 is indicative of the effectiveness of a CPR treatment and is determined by the processor 400 in part based on signals received from the sensors, e.g., force sensor 402 and accelerometers 404*a*, 404*b*.

The user interface module 408 can take one of several forms. In some implementations, the user interface module 408 is a combination of software and hardware and includes a display that presents information to a user of the device 100. For example, the information presented can include textual information and graphical information such as graphs and charts. The user interface module can also include other components such as input devices, e.g., buttons, keys, etc. In some implementations, the user interface module includes audio input/output elements, e.g., a microphone, speaker, and audio processing software.

In some implementations, the user interface module 408 causes a user interface to appear on an external device 412, e.g., a device that is capable of operating independent of the ACD device 100. For example, the external device could be a smartphone, tablet computer, or another mobile device. The external device could also be a defibrillator such as the ZOLL Medical Corp X-Series defibrillator (Chelmsford Mass.) with an accelerometer built into the defibrillation pads (CPR Stat-Padz), or other self-adhesive assembly containing a motion sensor that is adhered to the patient's sternum and measures primarily the motion of the patient's sternum. This assembly may or may not be integrated with the defibrillation electrodes. The defibrillator may receive the acceleration or motion data from the ACD device and compare the motion of the ACD sensor and compare it to the accelerometer or motion information from the accelerometer from the defibrillation pad or other adhered sternal motion-sensing assembly. If the two motions are found to differ by more than 0.25 in., for example, particularly during the decompression phase of the compression cycle, the rescuer may be prompted to reapply the ACD device.

In some implementations, the external device 412 communicates with the ACD device 100 using a wireless communication technique such as Bluetooth. In this example, the ACD device 100 has a wireless communication module 410. For example, the user interface module 408 may communicate signals to and from the external device 412 using the wireless communication module 410. Although Bluetooth is used as an example here, other wireless communications techniques could be used, such as WiFi, Zigbee, 802.11, etc.

In some implementations, the processor 400 can perform calculations to determine an estimate of chest compliance 414, e.g., using the equations described above with respect to FIG. 2.

In some implementations, the processor 400 can perform calculations to determine if a patient's chest was substantially released between two compressions (i.e., released sufficiently to create a pressure in the chest that facilitates venous filling of the heart). The user interface module 408 can cause a user interface 106 (FIG. 1) of the device 100 to display messages that give guidance or other feedback to the user 102 (FIG. 1), e.g., to more completely release the chest between compressions and/or to push harder on the chest during compression.

The processor 400 can further calculate an estimated neutral position of chest compression 416, e.g., based on data such as the estimated depth of chest compression and the estimate of chest compliance 414. The calculation can be based in part on a feature of a compliance relationship as described below in further detail with respect to FIGS. 5 and 6.

The output information 406 can include information determined based on the estimate of chest compliance 414 and the neutral position of chest compression 416. For example, the output information 406 could include information such as a compression non-elevated (CN) depth or decompression elevated (DE) height. The output information 406 can also include feedback to the user about adjusting the user's actions in a way that would increase the effectiveness of a CPR treatment. Examples are described below with respect to FIG. 7.

In some implementations, the processor 400 compares signals received by the first accelerometer 404a and the second accelerometer 404b. As described above with respect to FIG. 2, the first accelerometer 404a can be placed in or near a housing of the ACD device 100, and the second accelerometer 404b can be placed in or near a suction cup 112 of the ACD device 100. In this way, the first accelerometer 216b tends to measure acceleration experienced by the user 102 (FIG. 1), and the second accelerometer tends to measure acceleration experienced by the patient 104. In some implementations, multiple accelerometers 216b, 216c can be used. For example, the second accelerometer 216c can be placed on the patient's sternum in the inner perimeter or near the suction cup 112. The second accelerometer may be contained in a separate assembly of self-adhesive foam such as the ZOLL CPR Stat-Padz (Chelmsford, Mass.). In this way, the first accelerometer 216b tends to measure acceleration experienced by the rescuer's hands 102 (FIG. 1), and the second accelerometer 216c tends to measure acceleration of the patient's sternum 104. In this fashion, the system can detect if there is insufficient adherence between the ACD device and the patient's sternum and alert the rescuer to re-apply the ACD device to the patient's chest.

In some implementations, the processor 400 includes or has access to a memory 418 that can store data. The memory 418 can take any of several forms and may be integrated with the processor 400 (e.g., may be part of the same integrated circuit) or may be a separate component in communication with the processor 400 or may be a combination of both. In some implementations, the memory 418 stores data such as values for the estimate of chest compliance 414 and the neutral position of chest compression 416 as they are calculated by the processor 400. In some implementations, the processor 400 uses the memory 418 to store data for later retrieval, e.g., stores data during an administration of CPR for retrieval later during the same administration of CPR or for retrieval later during a different administration of CPR.

FIG. 5 shows an example graph 500 including a chest compliance curve 502. In some implementations, the compliance curve 502 is a representation of data calculated by the processor 400 (FIG. 4) based on input received from sensors, e.g., a force sensor and/or accelerometer(s). The graph 500 shown in FIG. 5 includes an x-axis representing time (e.g., in seconds) and a y-axis representing chest compliance. The curve 502 exhibits a sinusoidal shape. This kind of compliance curve 502 is sometimes called a non-hysteresis compliance curve.

In practical terms, when a rescuer is performing CPR on a victim using an ACD device (e.g., the device 100 shown in FIG. 1), the rescuer causes downward and upward forces to be exerted on the chest of the victim. The victim's chest compliance will be lowest as the forces cause the shape of the chest to approach its natural limits. In other words, the victim's chest compliance approaches a lower limit as it is pulled up or pulled down. In some scenarios, when the chest compliance approaches this lower limit it is an indication that the tensile strength of the ribs have been reached, and that if additional force is exerted, one or more ribs have an elevated risk of fracturing. In some versions of the system, a warning may be provided in the form of audio, visual or tactile/haptic prompts indicating that the compliance has been reduced below some threshold level.

Figure 6A:
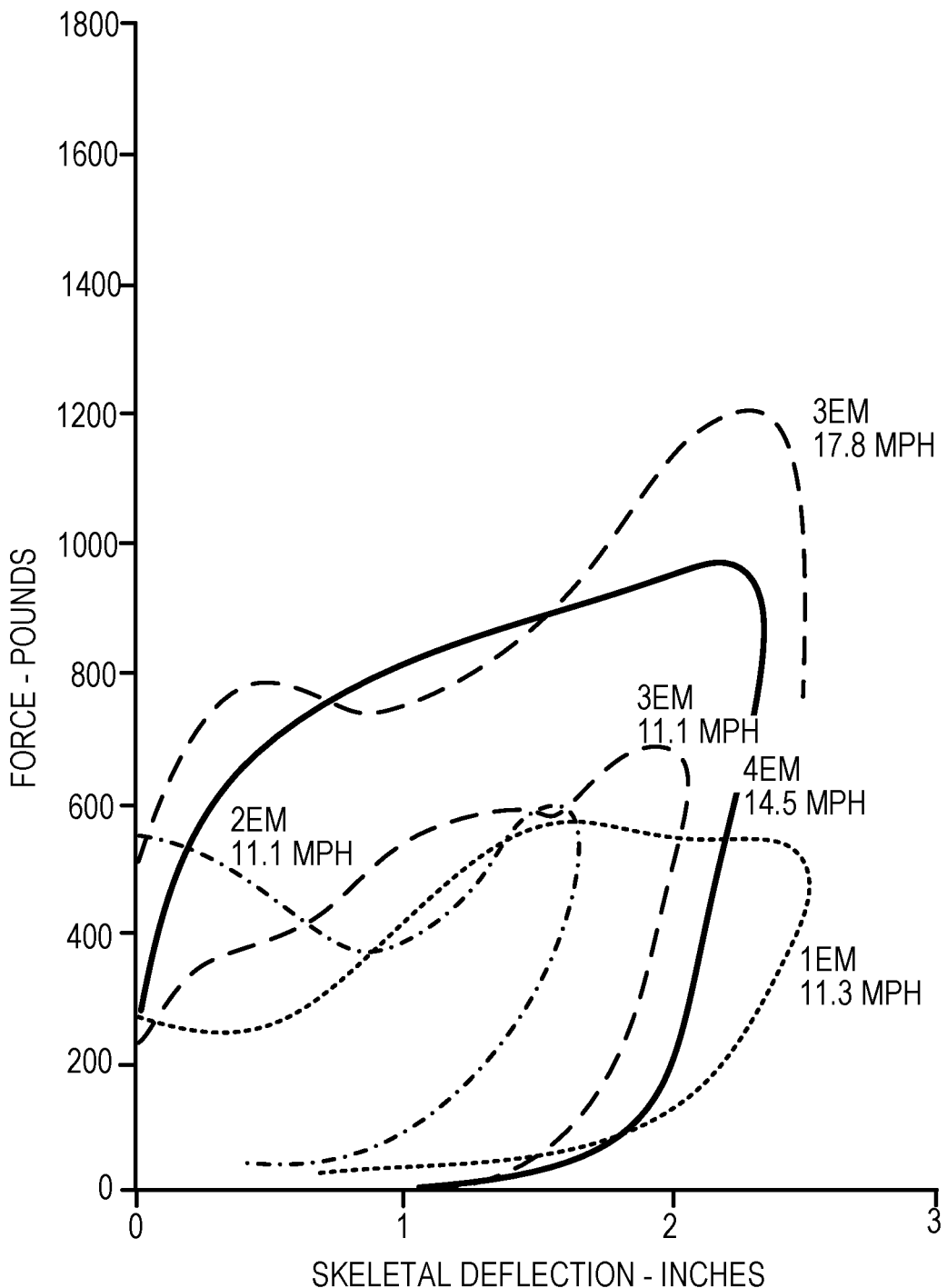
FIGS. 6A and 6B show graphs of stiffness curves.
Figure 6B:
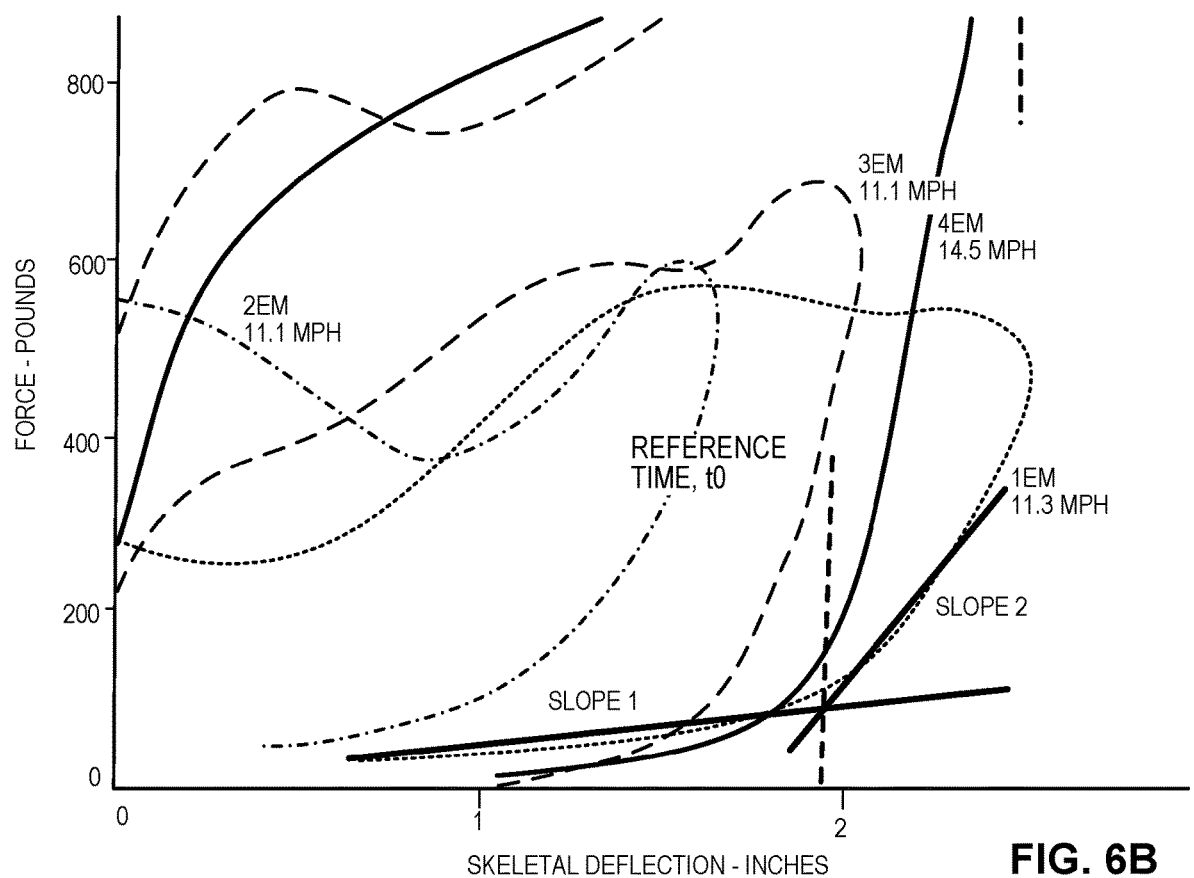

FIG. 6A shows representative stiffness curves for sternal impact, and FIG. 6B shows stiffness regions of the curves. Referring to these figures, the slopes of the representative curves are the stiffness (e.g., the inverse of compliance). Each of the loops is the curve for a different subject. Slope 1 in FIG. 6B is the stiffness for the CN phase of the compression; it is a lower slope value and less stiff (and thus higher compliance). Though the slopes for the CN phase of compression for each subject varies as seen in the multiple loops in the figure, in most if not all cases, there will be a change in slope to a second, steeper slope (lower compliance, and more stiff) at some inflection point during the compression, represented by the shift to Slope 2.

At the inflection point represented by the intersection of the two lines, Slope 1 and Slope 2 in the figure, the risk of fracturing is still relatively low. Once the inflection point has been detected, the system can prompt the rescuer to maintain that compression depth, as it is still in the safe range. This patient-specific compression depth will likely be different that AHA/ILCOR Guidelines (e.g. more than 2 inches). For instance, initially at the start of the resuscitation efforts, the patient's chest may be much stiffer, particularly for elderly patients, where their sternal cartilage attaching the sternum to the ribs has calcified and stiffened. If the rescuer were to try and deliver compressions at a depth recommended by the AHA/ILCOR Guidelines, they would likely cause rib fractures in the patient. In fact, in the Guidelines statement themselves, it is acknowledged that rib fractures are a common occurrence using existing chest compression methods. "Rib fractures and other injuries are common but acceptable consequences of CPR given the alternative of death from cardiac arrest." (From the 2005 International Consensus Conference on Cardiopulmonary Resuscitation and Emergency Cardiovascular Care Science with Treatment Recommendations, hosted by the American Heart Association in Dallas, Tex., Jan. 23-30, 2005.) Aside from the discomfort of the nosocomial rib fractures, an unfortunate side effect of the rib fractures is that they result in reduced resilience of the chest wall and thus a reduction in the natural recoil of the chest during the decompression phase resulting in a reduced venous return and degraded chest compression efficacy. It is desirable to minimize or eliminate rib fractures for these reasons. By detecting changes in the chest wall compliance, and prompting the rescuer as a result of those detections, chest compression depth will not exceed the injury threshold of ribs and sternum.

Because the neutral position as well as the overall compliance of the chest varies over the course of the resuscitation effort, the depth to which the rescuer is being guided by the real-time prompting of the system will also vary using this approach. A phenomena known as chest-wall remodeling occurs during the initial minutes subsequent to the initiation of chest compressions. AP diameter may decrease by as much as 0.5-1 inch, and compliance of the chest wall will increase as the sternal cartilage is gradually softened. By staying within the safety limits in a customized fashion for each individual patient for each compression cycle as the chest gradually softens, injuries are reduced, but more importantly, the natural resilience of the chest wall is maintained and more efficacious chest compressions are delivered to the patient.

Generally speaking, methods for detecting the change in slope can include determining initial statistical characteristics of the slope of the CE phase, and then analyzing the slope for any significant, sustained increase in slope. For instance, techniques can be used such as change point analysis such as that described by Basseville (Basseville M, Nikiforov I V. Detection of Abrupt Changes: Theory and Application. Engelwood, N.J.: Prentice-Hall 1993) or Pettitt (Pettitt AN) A simple cumulative sum type statistic for the change point problem with zero-one observations. (Biometrika 1980; 67:79-84.) Other methods such as Shewhart control charts may be employed for first detecting changes in the slope and then assessing whether the change detected is both an increase and of a sufficient magnitude to generate a prompt to the rescuer indicating that the depth of compression is too deep, and in some way to compress less deeply for future compressions. In simpler versions, prompting may be initiated when the compliance decreases below some percentage threshold below the initial compliance values at the start of a particular compression, e.g. 15% reduction in compliance. The initial compliance value may be averaged over more than one compression phase; it may be used as a comparative value for multiple compression cycles.

In some embodiments, separate tests may be performed on compliance to determine risk of injury during both the DE phase and the CN phase (i.e. at the top of the decompression portion [DN and DE phases] of the compression cycle and the bottom of the compression portion [CE and CN phases] of the compression cycle.)

In contrast, when the victim's chest is at a neutral position of chest compression (generally corresponding to the natural resting position of the chest), chest compliance tends to be at its highest point. Thus, in the curve 502 shown in FIG. 5, the points 504, 506 corresponding to the highest chest compliance (e.g., the peaks of the sinusoid) tend to correspond to the neutral position of chest compression. In contrast, the points 508 correspond to the lowest chest compliance (e.g., the troughs of the sinusoid) tend to correspond to the limits of the chest's compression shape or decompression shape.

In some implementations, the processor 400 (FIG. 4) can use a feature of the non-hysteresis compliance curve 502 to calculate an estimate of the neutral position of chest compression 416 (FIG. 4). For example, the processor 400 can use peaks 504, 506 of the curve 502 to calculate an estimate of the neutral position of chest compression.

Figure 7:
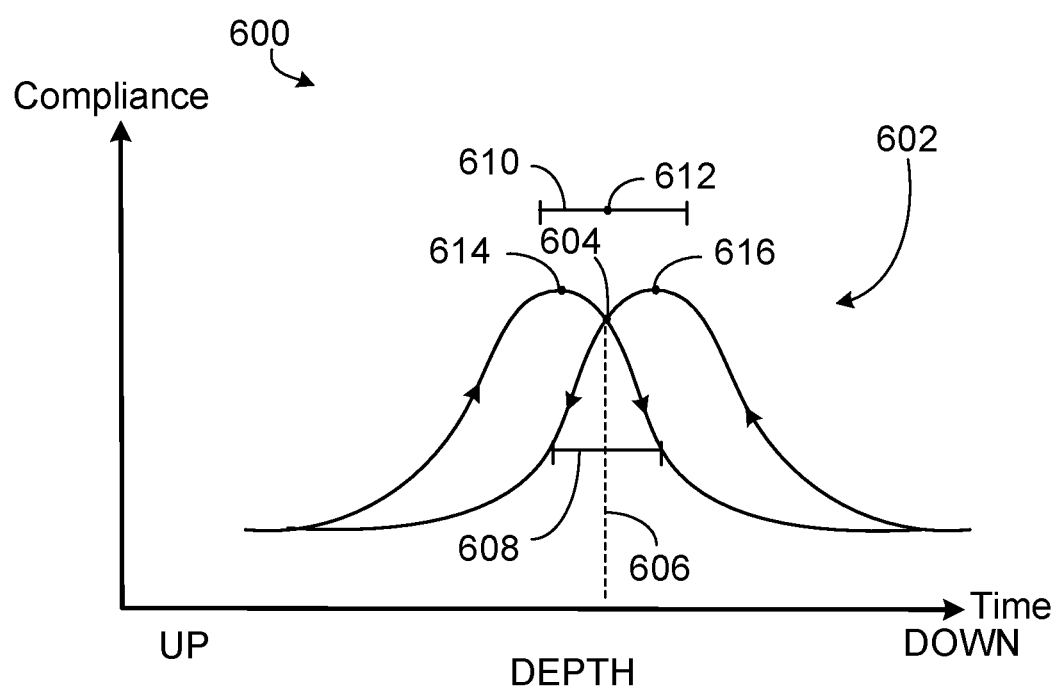
FIG. 7 shows an example graph including a chest compliance curve that forms a hysteresis loop.

FIG. 7 shows an example graph 600 including a chest compliance curve 602 that forms a hysteresis loop. This kind of compliance curve 602 is sometimes called a hysteretic compliance curve. In some implementations, the compliance curve 502 is a representation of data calculated by the processor 400 (FIG. 4) based on input received from sensors, e.g., a force sensor and/or motion sensor(s), e.g. accelerometer(s). The graph 600 shown in FIG. 7 includes an x-axis representing depth (e.g., in centimeters) and a y-axis representing chest compliance. The arrows on the curve show the progress of time during the course of one compression cycle, and represent the motion of the ACD device 100 (FIG. 1), for instance, the portion of the curve with the arrows pointing to the right show the instantaneous compliance (IC) for the compression portion (CE and CN) of the compression cycle, and the portion of the curve with leftward-facing arrows show the instantaneous compliance (IC) for the decompression portion (DE and DN) of the compression cycle. For example, when the ACD device 100 moves from a high depth to a low depth, chest compliance increases (as the chest approaches a neutral position of compression) and then decreases (as the chest becomes more compressed). Then, when the ACD device 100 moves from its lowest depth back to a high depth, chest compliance again increases (as the chest approaches a neutral position of compression) and again decreases (as the chest becomes more decompressed).

In some implementations, the processor 400 (FIG. 4) can use a feature of the hysteresis compliance curve 602 to calculate an estimate of the neutral position of chest compression 416 (FIG. 4). One of several features could be used.

For example, the point 604 of intersection of the hysteresis compliance curve 602 can be used to estimate the neutral position of chest compression 416. This point 604 represents a depth (e.g., as a coordinate of the x-axis) that may correspond to the neutral position of chest compression.

As another example, a point 612 approximately halfway between two peaks 614, 616 of the hysteresis compliance curve 602 can be used to estimate the neutral position of chest compression 416. The point 612 can be determined, for example, by measuring the distance 610 between the peaks 614, 616 and determining the point corresponding to the center of the distance 610. Alternative, the neutral point may be a point corresponding to a predefined percentage of the distance 610.

As another example, a point 606 approximately halfway between other features of the hysteresis compliance curve 602 can be used to estimate the neutral position of chest compression 416. For example, the processor could identify a distance 608 between two points of the hysteresis compliance curve 602 having the same value for compliance and then the point 606 can be calculated by determining the point corresponding to the center of the distance 608.

Figure 8:
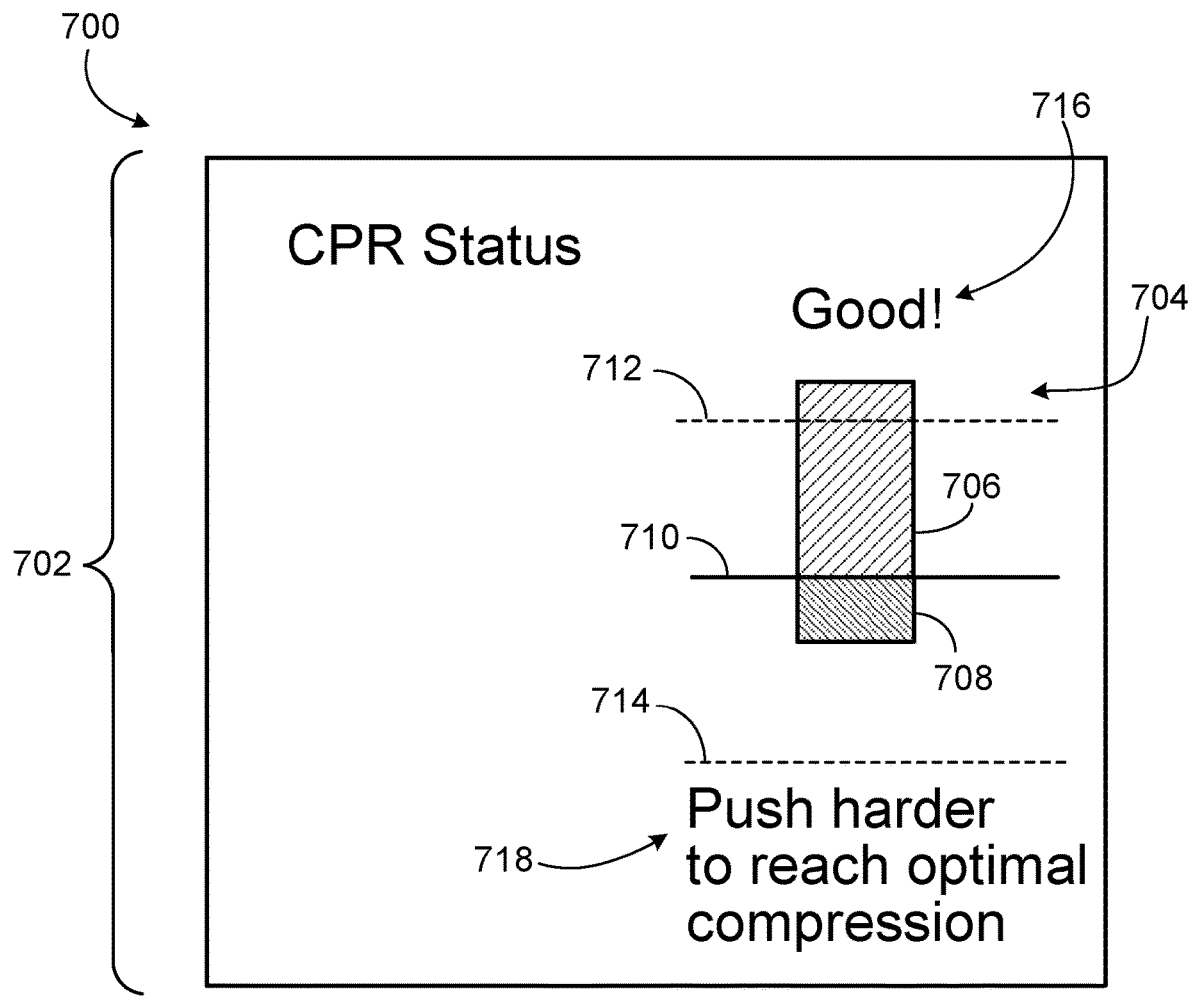
FIG. 8 shows an example of a user interface.

FIG. 8 shows an example of a user interface 700. For example, the user interface 700 may be an example of the user interface 106 of the ACD device shown in FIG. 1. Further, the user interface 700 may be controlled by the user interface module 408 shown in FIG. 4.

The user interface 700 displays information 702 representing effectiveness of a CPR treatment. The information 702 is displayed in a manner that enables a user 102 of the ACD device 100 (FIG. 1) to administer the CPR treatment effectively.

The information 702 includes a graph 704 representing the DE height 706 and CN depth 708 of the CPR treatment. The depth and height are separated by a boundary 710. In some implementations, the DE height 706 and CN depth 708 are determined by the processor 400 (FIG. 4). For example, the DE height 706 and CN depth 708 can be calculated using information the accelerometer(s) 404a-404b and knowing the time of occurrence of the peak heights and depths along with the neutral position. Alternatively, DE height and CN depth can be estimated from the force sensor 402 including calculated information such as the estimate of chest compliance 414 and the neutral position of chest compression 416 determined by the processor 400. Alternatively, the DE portion 706 of the display feedback or the CN portion 708 may display measurements of pressure rather than displacement. For instance, in one embodiment, the DE portion 706 may display a measure of pressure or force, DE force, while the CN portion 708 may display a measure of displacement, CN depth.

Figure 9:
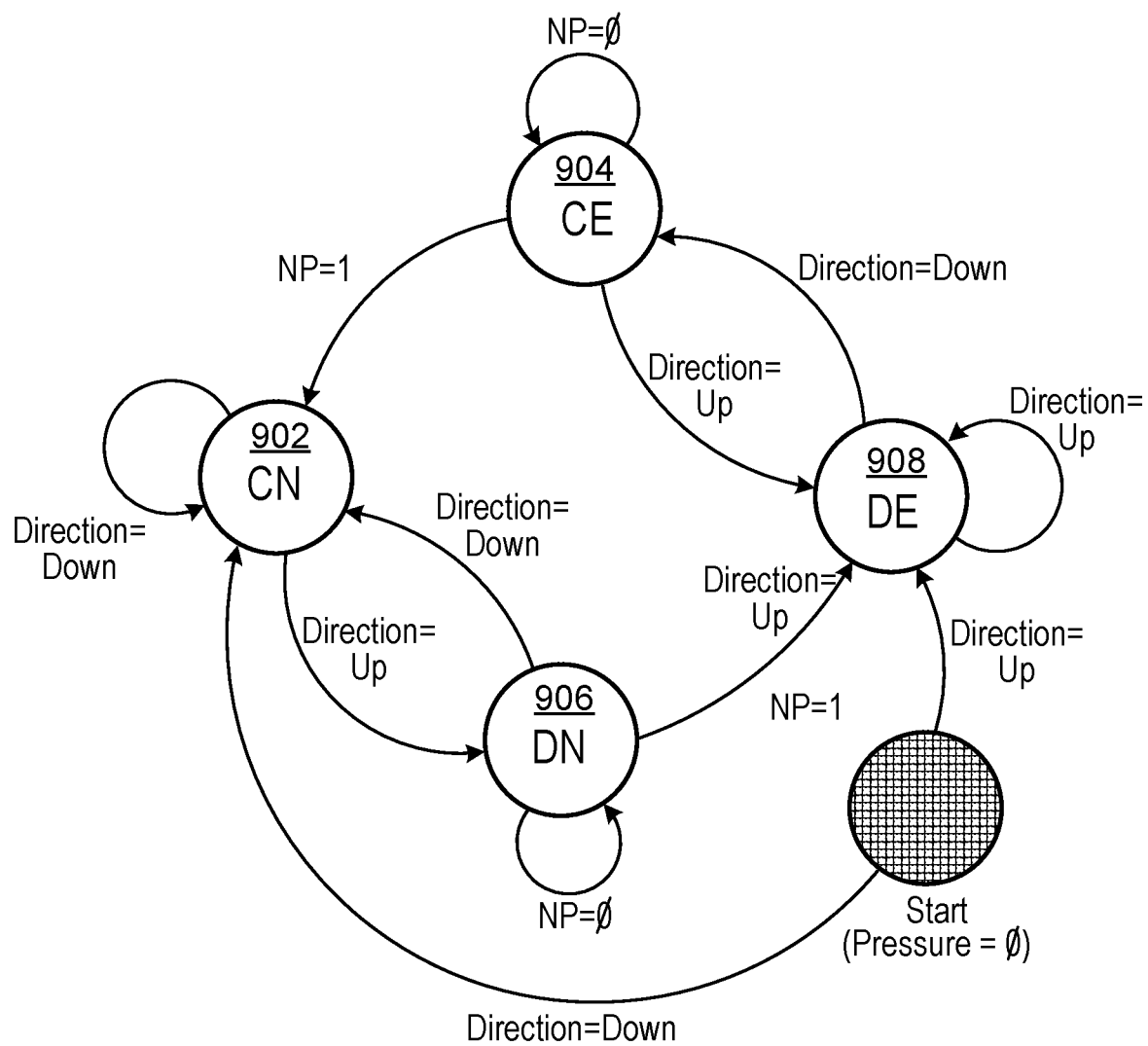
FIG. 9 shows a state transition diagram of a chest compression cycle.

Referring to FIG. 9, in some examples, a state transition diagram may be used to determine the phases of the compression cycle (e.g. CN, DN, DE and CE phases) based on inputs of compression direction (i.e. DE or CN) and whether the neutral point 416 has been reached. Transitions from CE 904 to CN 902 phases and DN 906 to DE 908 phases with the detection of a neutral position (NP). Upon transition to either CN 902 or DE 908, NP is reset to 0, i.e. the transition is edge sensitive. Transitions on direction are level sensitive. Transitions from CN 902 to DN 906 and DE 908 to CE 904 occur on change in direction. Parameters descriptive of the motion, such as velocity, distance, average velocity, peak velocity, etc., may be calculated knowing the time of occurrence of the transition between the compression phase states. In some versions, information 702 may also include other motion information may be displayed, such as velocity occurring during the decompression phase. More specifically, the velocity at the time that the neutral position occurs may be displayed, or otherwise communicated to the rescuer (e.g. tones, verbal, etc.). Alternatively, the velocity communicated to the rescuer may be an average or other statistical representation of the motion during a significant portion of the decompression phase (both elevated and non-elevated portions).

Referring to FIG. 8, the graph 704 also includes a DE height threshold indicator 712 and a CN depth threshold indicator 714. These indicators provide information to a user of the device about whether either or both of the DE height and CN depth is too shallow or too deep. For example, if the user sees that the DE height 706 does not meet the threshold indicator 712, the user can adjust his or her motion to increase the DE height (e.g., by pulling the ACD device with greater force during the DE motion). Similarly, if the user sees that the DE height indicator 706 passes the threshold indicator 712, the user can adjust his or her motion to decrease the DE height (e.g., by pulling the ACD device with less force during the DE motion). The user can similarly adjust the force during the CN motion if the user sees that the CN depth 708 does not meet the threshold indicator 714.

Further, the information 702 can include guidance displayed to the user based on the thresholds represented by the indicators 712, 714. For example, if either the DE depth or CN depth is not within a certain range of the threshold (e.g., more than 10% greater or 10% less than the threshold), then the user interface 700 can display messages guiding the user. In the example shown in FIG. 8, the CN depth indicator 708 indicates that the CN depth falls far short of the CN threshold indicator 714. In response, the user interface 700 displays a message 718 to the user indicating that he or she should push harder to reach optimal compression. A similar message could be displayed (with respect to optimal decompression) if the DE height indicator 706 fell short of its respective threshold. Similarly, if the DE height 706 or the CN depth 708 passed its respective threshold by a substantial amount (e.g., more than 10% past the threshold indicator), the user interface 700 could display a warning message (e.g., "reduce CN force to avoid injuring the patient").

Alternatively, a miniature vibrator such as used in all cell phones, may be included in the assembly in physical contact with the rescuer's hands, and haptic feedback about correct CN depth and DE height can be communicated, e.g. it vibrates when the thresholds are achieved.

In the example shown in FIG. 8, the DE height indicator 706 is close to the DE threshold indicator 712. Thus, the user interface 700 displays a message 718 indicating that the user is using an appropriate amount of force on DE motions.

In some implementations, the threshold indicators 712, 714 are displayed based on thresholds that are static values. For example, the memory 418 of the processor 400 (FIG. 4) may store static values, e.g., based on experimental data about DE height and CN depth in patients. The static values could be used directly, or the values may be modified by a variable measured with respect to the patient receiving the CPR treatment.

In some implementations, the threshold indicators 712, 714 are displayed based on thresholds calculated by a processor, e.g., the processor 400 shown in FIG. 4. In some examples, the calculated thresholds are based on a calculation of chest compliance, e.g., the estimate of chest compliance 414 shown in FIG. 4. For example, referring to the compliance curve 602 shown in FIG. 7, values of depth corresponding to the lowest values of chest compliance may correspond to the maximum DE height and maximum CN depth.

Figure 10:
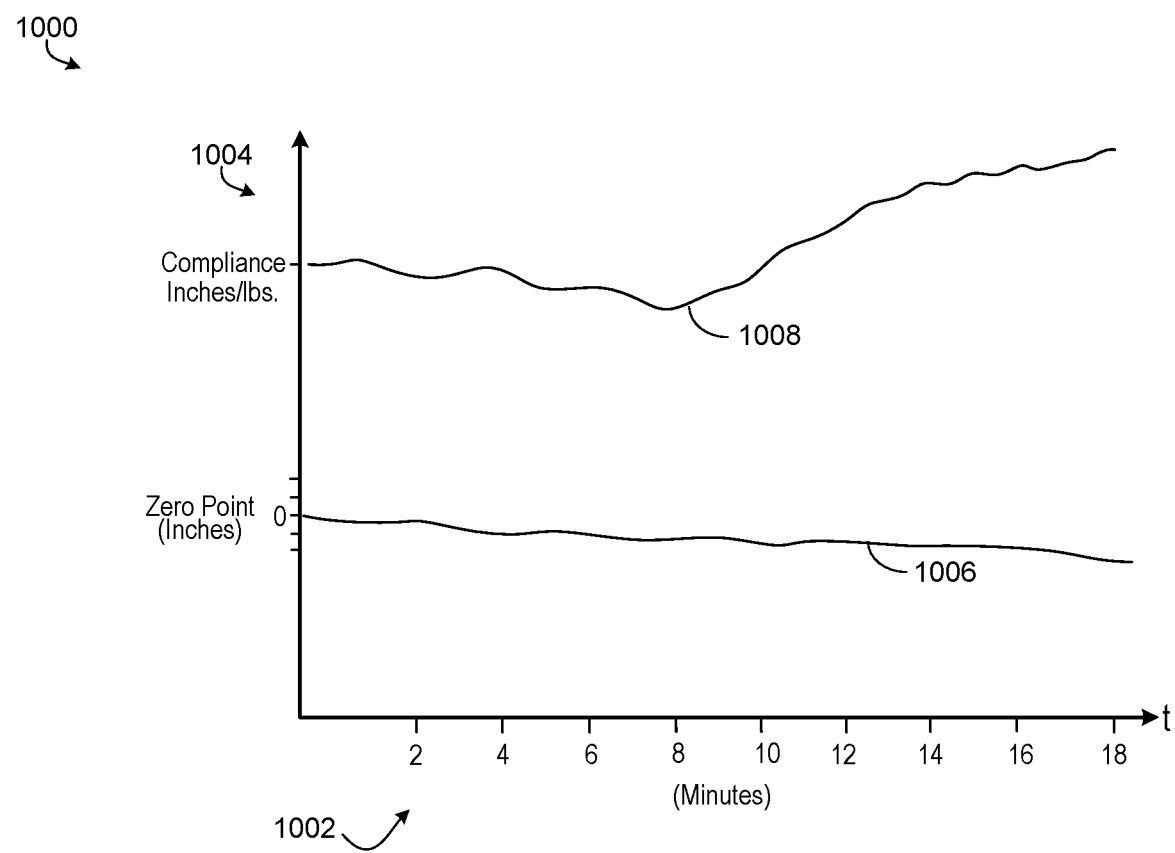
FIG. 10 shows a trend graph of chest remodeling.

In some implementations, the user interface 700 shows a trend graph representing chest remodeling. For example, the trend graph can represent what happens to the patient's chest over the course of a CPR treatment. FIG. 10 shows an example of the trend graph 1000 that could be displayed on the user interface 700. The trend graph 1000 has an x-axis 1002 representing time and a y-axis 1004 representing compliance. As shown in the example in the figure, the trend graph 1000 can include a zero point trend line 1006 (e.g., a trend line representing a starting depth of the patient's chest) and a compliance trend line 1008. Over time, the zero point and the compliance change as a CPR treatment is delivered, as represented by the trend graph.

Figure 11:
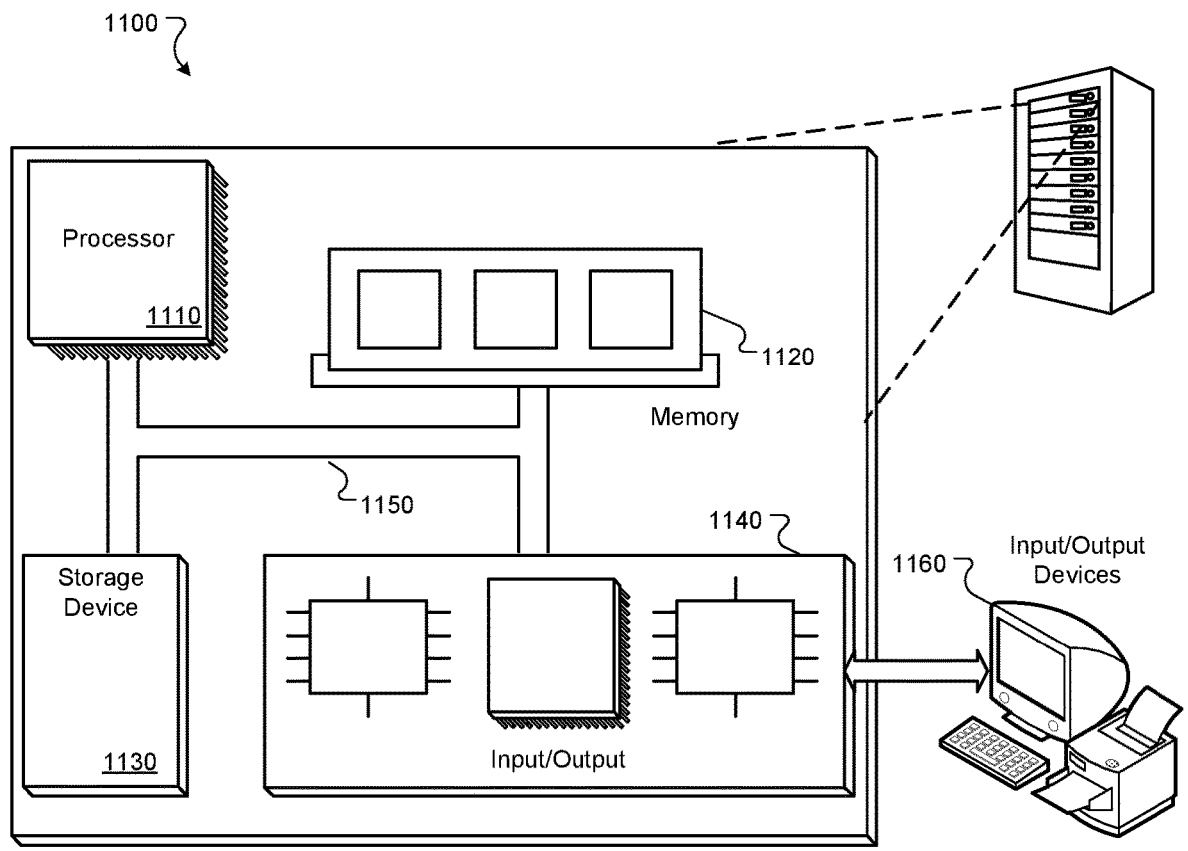
FIG. 11 is a block diagram of an example computer system.

FIG. 11 is a block diagram of an example computer system 1100. For example, referring to FIG. 1, the ACD device 100 could be an example of the system 1100 described here, as could the external device 412 (FIG. 4). The system 1100 includes a processor 1110, a memory 1120, a storage device 1130, and one or more input/output interface devices 1140. Each of the components 1110, 1120, 1130, and 1140 can be interconnected, for example, using a system bus 1150.

The processor 1110 may be an example of the processor 400 shown in FIG. 4 and is capable of processing instructions for execution within the system 1100. The term "execution" as used here refers to a technique in which program code causes a processor to carry out one or more processor instructions. In some implementations, the processor 1110 is a single-threaded processor. In some implementations, the processor 1110 is a multi-threaded processor. In some implementations, the processor 1110 is a quantum computer. The processor 1110 is capable of processing instructions stored in the memory 1120 or on the storage device 1130. The processor 1110 may execute operations such as determining a neutral position of chest compression based at least in part on a feature of a compliance curve.

The memory 1120 stores information within the system 1100. In some implementations, the memory 1120 is a computer-readable medium. In some implementations, the memory 1120 is a volatile memory unit. In some implementations, the memory 1120 is a non-volatile memory unit.

The storage device 1130 is capable of providing mass storage for the system 1100. In some implementations, the storage device 1130 is a non-transitory computer-readable medium. In various different implementations, the storage device 1130 can include, for example, a hard disk device, an optical disk device, a solid-date drive, a flash drive, magnetic tape, or some other large capacity storage device. In some implementations, the storage device 1130 may be a cloud storage device, e.g., a logical storage device including one or more physical storage devices distributed on a network and accessed using a network. In some examples, the storage device may store long-term data. The input/output interface devices 1140 provide input/output operations for the system 1100. In some implementations, the input/output interface devices 1140 can include one or more of a network interface devices, e.g., the wireless communication module 410 shown in FIG. 4, or an Ethernet interface, a serial communication device, e.g., an RS-232 interface, and/or a wireless interface device, e.g., an 802.11 interface, a 3G wireless modem, a 4G wireless modem, etc. A network interface device allows the system 1100 to communicate, for example, transmit and receive data. In some implementations, the input/output device can include driver devices configured to receive input data and send output data to other input/output devices, e.g., keyboard, printer and display devices 1160. In some implementations, mobile computing devices, mobile communication devices, and other devices can be used.

Referring to FIG. 4, steps carried out by the processor 400 can be realized by instructions that upon execution cause one or more processing devices to carry out the processes and functions described above, for example, determining information relevant to a CPR treatment. Such instructions can include, for example, interpreted instructions such as script instructions, or executable code, or other instructions stored in a computer readable medium.

A computer system 1100 can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the system 1100 is contained within a single integrated circuit package. A system 1100 of this kind, in which both a processor 1110 and one or more other components are contained within a single integrated circuit package and/or fabricated as a single integrated circuit, is sometimes called a microcontroller. In some implementations, the integrated circuit package includes pins that correspond to input/output ports, e.g., that can be used to communicate signals to and from one or more of the input/output interface devices 1140.

Although an example processing system has been described in FIG. 11, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server (e.g., is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. Accordingly, other embodiments are within the scope of the following claims.

What is claimed is:

1. A method for assisting with cardiopulmonary resuscitation (CPR) administered to a patient using an active compression-decompression device, the method comprising:

receiving, from at least one motion sensor and from at least one force sensor, data recorded during administration of active compression-decompressions to the chest of the patient by the active compression-decompression device;

calculating a chest compliance relationship during the active compression-decompressions involving displacement and force based on the data received from the at least one motion sensor and the at least one force sensor;

estimating a neutral position of the chest for a cycle of the active compression-decompressions as the active compression-decompressions of the cycle are administered, the neutral position of the chest being based at least in part on a feature of the chest compliance relationship, wherein the cycle comprises a continuous variation from a non-elevated chest position to an elevated decompressed chest position and the neutral position of the chest corresponds to a transition phase of the cycle of the active compression-decompressions during which the force applied to the chest is substantially zero; and adjusting one or more application parameters of the active compression-decompression device based on the neutral position of the chest.

2. The method of claim 1, wherein the one or more application parameters comprise at least one of displacement, velocity, acceleration, time, work, power, pressure, direction and orientation.

3. The method of claim 1, wherein the one or more application parameters comprise a distance above the neutral position of the chest and a depth of compression below the neutral position of the chest.

4. The method of claim 1, wherein the chest compliance relationship defines a compliance curve.

5. The method of claim 4, wherein the compliance curve comprises a hysteresis compliance curve illustrating a chest compliance relative to a chest compression displacement.

6. The method of claim 5, wherein the feature of the hysteresis compliance curve comprises a point of intersection of subsequent hysteresis compliance curves.

7. The method of claim 4, wherein the feature of the compliance curve comprises a point approximately halfway between two peaks of two compliance curves.

8. The method of claim 4, wherein the compliance curve comprises a non-hysteresis compliance curve.

9. The method of claim 4, wherein the feature comprises a peak of the compliance curve.

10. The method of claim 1, wherein adjusting one or more application parameters of the active compression-decompression device based on the neutral position of the chest comprises:

increasing the one or more application parameters of the active compression-decompression device, or decreasing the one or more application parameters of the active compression-decompression device.

11. The method of claim 1, wherein adjusting one or more application parameters of the active compression-decompression device based on the neutral position of the chest comprises providing an output for a user to adjust the one or more application parameters.

12. The method of claim 1, wherein the data recorded during administration of the active compression-decompressions to the chest of the patient comprises a pressure measurement.

13. The method of claim 1, wherein the data recorded during administration of the active compression-decompressions to the chest of the patient comprises a displacement signal.

14. The method of claim 1, wherein the data recorded during administration of the active compression-decompressions to the chest of the patient comprises information for determining whether at least one transition point of the CPR has been reached.

15. The method of claim 14, wherein the at least one transition point is at least one of between an elevated compression phase and a non-elevated compression phase, between an elevated decompression phase and the elevated compression phase, between the elevated decompression phase and a hold time above the neutral position of the chest, and between a hold time above the neutral position of the chest and the elevated compression phase.

16. The method of claim 14, wherein the at least one transition point is at least one of between a non-elevated compression phase and a non-elevated decompression phase, between the non-elevated compression phase and a hold time below the neutral position of the chest, and between hold time below the neutral position of the chest and the non-elevated decompression phase.

17. The method of claim 14, wherein the at least one transition point is between a non-elevated decompression phase and an elevated decompression phase.

18. The method of claim 1 comprising:
identifying a potential for injury of a patient undergoing CPR, the identification based at least in part on the feature of the chest compliance relationship.

19. The method of claim 18, wherein a reduction in compliance below a predetermined threshold indicates the potential for injury of the patient undergoing CPR.

20. The method of claim 1 comprising:
applying a negative pressure on the chest of the patient.

21. The method of claim 1, wherein the neutral position of the chest comprises a first neutral position of the chest corresponding to a first chest compression of the chest that is different from a second neutral position of the chest corresponding to a second chest compression that is subsequent to the first chest compression.

22. A system for assisting with cardiopulmonary resuscitation (CPR), the system comprising:
an active compression-decompression device configured to be affixed to a chest of a patient, the active compression-decompression device being configured to deliver active compression-decompressions to the chest of the patient;
at least one motion sensor operably coupled with the active compression-decompression device;
at least one force sensor operably coupled with the active compression-decompression device; and
one or more processors and a non-transitory computer readable storage medium encoded with a computer program comprising instructions that, when executed, cause the one or more processors to perform operations comprising:
calculating a chest compliance relationship during the active compression-decompressions involving displacement and force based on data received from the at least one motion sensor and the at least one force sensor,
estimating a neutral position of the chest for a cycle of the active compression-decompressions as the active compression-decompressions of the cycle are administered, the neutral position of the chest being based at least in part on a feature of the chest compliance relationship, wherein the cycle comprises a continuous variation from a non-elevated chest position to an elevated decompressed chest position and the neutral position of the chest corresponds to a transition phase of the cycle of the active compression-decompressions during which the force applied to the chest is substantially zero, and
generating an indication to adjust one or more application parameters of the active compression-decompression device based on the neutral position of the chest.

23. The system of claim 22, wherein the one or more application parameters comprise at least one of displacement, velocity, acceleration, time, work, power, pressure, direction and orientation.

24. The system of claim 22, wherein the one or more application parameters comprise a distance above the neutral position of the chest and a depth of compression below the neutral position of the chest.

25. The system of claim 22, wherein the chest compliance relationship defines a compliance curve.

26. The system of claim 25, wherein the compliance curve comprises a hysteresis compliance curve illustrating a chest compliance relative to a chest compression displacement.

27. The system of claim 26, wherein a feature of the hysteresis compliance curve comprises a point of intersection of subsequent hysteresis compliance curves.

28. The system of claim 26, wherein the feature of the compliance curve comprises a point approximately halfway between two peaks of two compliance curves.

29. The system of claim 25, wherein the compliance curve comprises a non-hysteresis compliance curve.

30. The system of claim 29, wherein the feature comprises a peak of the non-hysteresis compliance curve.

31. The system of claim 22, wherein the active compression-decompression device comprises a suction cup and a handle.

32. The system of claim 22, wherein the at least one force sensor provides an output convertible to a pressure measurement.

33. The system of claim 22, wherein at least one of the at least one motion sensor and the at least one force sensor are components of the active compression-decompression device.

34. The system of claim 22, wherein the at least one motion sensor comprises an accelerometer.

35. The system of claim 22, wherein the at least one motion sensor measures information for determining whether at least one transition point of the CPR has been reached.

36. The system of claim 35, wherein the at least one transition point is at least one of between an elevated compression phase and a non-elevated compression phase, between an elevated decompression phase and the elevated compression phase, between the elevated decompression phase and a hold time above the neutral position of the chest, and between a hold time above the neutral position of the chest and the elevated compression phase.

37. The system of claim 35, wherein the at least one transition point is at least one of between a non-elevated compression phase and a non-elevated decompression phase, between the non-elevated compression phase and a hold time below the neutral position of the chest, and between hold time below the neutral position of the chest and the non-elevated decompression phase.

38. The system of claim 35, wherein the at least one transition point is between a non-elevated decompression phase and an elevated decompression phase.

39. The system of claim 22, wherein the one or more processors are configured for identifying a potential for injury of a patient undergoing CPR, the identification based at least in part on the feature of the chest compliance relationship.

40. The system of claim 39, wherein a reduction in compliance below a predetermined threshold indicates the potential for injury of the patient undergoing CPR.

41. The system of claim 22, wherein the system comprises an impedance threshold device configured to apply negative pressure on the chest of the patient.

42. The system of claim 22, wherein the system comprises an adhesive pad configured to be adhered to at least a portion of a patient's chest.

43. The system of claim 22, wherein the neutral position of the chest comprises a first neutral position of the chest corresponding to a first chest compression of the chest that is different from a second neutral position of the chest corresponding to a second chest compression that is subsequent to the first chest compression.

44. A method for assisting with cardiopulmonary resuscitation (CPR) administered to a patient using an active compression-decompression device, the method comprising:
 receiving, from at least one motion sensor and from at least one force sensor, data recorded during administration of active compression-decompressions to the chest of the patient by the active compression-decompression device;
 calculating a chest compliance relationship during the active compression-decompressions involving displacement and force based on the data received from the at least one motion sensor and the at least one force sensor;
 estimating a neutral position of the chest for a cycle of the active compression-decompressions as the active compression-decompressions of the cycle are administered, the cycle comprising a continuous variation from a non-elevated chest position to an elevated compressed chest position, the neutral position of the chest being based at least in part on a feature of the chest compliance relationship; and
 adjusting one or more application parameters of the active compression-decompression device based on the neutral position of the chest.

45. The method of claim 44, wherein the one or more application parameters comprise at least one of displacement, velocity, acceleration, time, work, power, pressure, direction orientation, and a distance above the neutral position of the chest and a depth of compression below the neutral position of the chest.

46. The method of claim 44, wherein the chest compliance relationship defines a compliance curve.

47. The method of claim 46, wherein the compliance curve comprises a hysteresis compliance curve illustrating a chest compliance relative to a chest compression displacement, wherein the feature of the hysteresis compliance curve comprises a point of intersection of subsequent hysteresis compliance curves.

48. The method of claim 46, wherein the feature of the compliance curve comprises a point approximately halfway between two peaks of two compliance curves.

49. The method of claim 46, wherein the compliance curve comprises a non-hysteresis compliance curve.

50. The method of claim 49, wherein the feature comprises a peak of the compliance curve.

51. The method of claim 44, wherein adjusting one or more application parameters of the active compression-decompression device based on the neutral position of the chest comprises:
 increasing the one or more application parameters of the active compression-decompression device, or
 decreasing the one or more application parameters of the active compression-decompression device.

52. The method of claim 44, wherein adjusting one or more application parameters of the active compression-decompression device based on the neutral position of the chest comprises providing an output for a user to adjust the one or more application parameters.

53. The method of claim 44, wherein the data recorded during administration of the active compression-decompressions to the chest of the patient comprises a pressure measurement or a displacement signal.

54. The method of claim 44, wherein the data recorded during administration of the active compression-decompressions to the chest of the patient comprises information for determining whether at least one transition point of the CPR has been reached.

55. The method of claim 54, wherein the at least one transition point is at least one of between an elevated compression phase and a non-elevated compression phase, between an elevated decompression phase and the elevated compression phase, between the elevated decompression phase and a hold time above the neutral position of the chest, and between a hold time above the neutral position of the chest and the elevated compression phase.

56. The method of claim 54, wherein the at least one transition point is at least one of between a non-elevated compression phase and a non-elevated decompression phase, between the non-elevated compression phase and a hold time below the neutral position of the chest, and between hold time below the neutral position of the chest and the non-elevated decompression phase.

57. The method of claim 54, wherein the at least one transition point is between a non-elevated decompression phase and an elevated decompression phase.

58. The method of claim 44 comprising:
 identifying a potential for injury of a patient undergoing CPR, the identification based at least in part on the feature of the chest compliance relationship, wherein a reduction in compliance below a predetermined threshold indicates the potential for injury of the patient undergoing CPR.

59. The method of claim 44 comprising:
 applying a negative pressure on the chest of the patient.

60. The method of claim 44, wherein the neutral position of the chest comprises a first neutral position of the chest corresponding to a first chest compression of the chest that is different from a second neutral position of the chest corresponding to a second chest compression that is subsequent to the first chest compression.

61. A system for assisting with cardiopulmonary resuscitation (CPR), the system comprising:
 an active compression-decompression device configured to be affixed to a chest of a patient, the active compression-decompression device being configured to deliver active compression-decompressions to the chest of the patient;
 at least one motion sensor operably coupled with the active compression-decompression device;
 at least one force sensor operably coupled with the active compression-decompression device; and
 one or more processors and a non-transitory computer readable storage medium encoded with a computer program comprising instructions that, when executed, cause the one or more processors to perform operations comprising:
  calculating a chest compliance relationship during the active compression-decompressions involving displacement and force based on data received from the at least one motion sensor and the at least one force sensor, estimating a neutral position of the chest for a cycle of the active compression-decompressions as the active compression-decompressions of the cycle are administered, wherein the cycle comprises a continuous variation from a non-elevated chest position to an elevated decompressed chest position, the neutral position of the chest being based at least in part on a feature of the chest compliance relationship, and generating an indicator to adjust one or more application parameters of the active compression-decompression device based on the neutral position of the chest.

62. The system of claim 61, wherein the one or more application parameters comprise at least one of displacement, velocity, acceleration, time, work, power, pressure, direction orientation, and a distance above the neutral position of the chest and a depth of compression below the neutral position of the chest.

63. The system of claim 61, wherein the chest compliance relationship defines a compliance curve or a hysteresis compliance curve illustrating a chest compliance relative to a chest compression displacement.

64. The system of claim 63, wherein a feature of the hysteresis compliance curve comprises a first point of intersection of subsequent hysteresis compliance curves or a second point approximately halfway between two peaks of two compliance curves.

65. The system of claim 63, wherein the compliance curve comprises a non-hysteresis compliance curve, wherein the feature comprises a peak of the non-hysteresis compliance curve.

66. The system of claim 61, wherein the active compression-decompression device comprises a suction cup and a handle.

67. The system of claim 61, wherein the at least one force sensor provides an output convertible to a pressure measurement.

68. The system of claim 61, wherein at least one of the at least one motion sensor and the at least one force sensor are components of the active compression-decompression device.

69. The system of claim 61, wherein the at least one motion sensor comprises an accelerometer that measures information for determining whether at least one transition point of the CPR has been reached.

70. The system of claim 69, wherein the at least one transition point is at least one of between an elevated compression phase and a non-elevated compression phase, between an elevated decompression phase and the elevated compression phase, between the elevated decompression phase and a hold time above the neutral position of the chest, and between a hold time above the neutral position of the chest and the elevated compression phase.

71. The system of claim 70, wherein the at least one transition point is at least one of between a non-elevated compression phase and a non-elevated decompression phase, between the non-elevated compression phase and a hold time below the neutral position of the chest, and between hold time below the neutral position of the chest and the non-elevated decompression phase.

72. The system of claim 70, wherein the at least one transition point is between a non-elevated decompression phase and an elevated decompression phase.

73. The system of claim 61, wherein the one or more processors are configured for identifying a potential for injury of a patient undergoing CPR, the identification based at least in part on the feature of the chest compliance relationship, wherein a reduction in compliance below a predetermined threshold indicates the potential for injury of the patient undergoing CPR.

74. The system of claim 61, wherein the system comprises an impedance threshold device configured to apply negative pressure on the chest of the patient and an adhesive pad configured to be adhered to at least a portion of a patient's chest.

75. The system of claim 61, wherein the neutral position of the chest comprises a first neutral position of the chest corresponding to a first chest compression of the chest that is different from a second neutral position of the chest corresponding to a second chest compression that is subsequent to the first chest compression.

* * * * *